United States Patent
Jönsson

(10) Patent No.: US 8,803,093 B2
(45) Date of Patent: Aug. 12, 2014

(54) INFRARED CAMERA FOR GAS DETECTION

(75) Inventor: Henrik Jönsson, Stockholm (SE)

(73) Assignee: FLIR Systems AB, Taby (SE)

( * ) Notice: Subject to any disclaimer, the term of this patent is extended or adjusted under 35 U.S.C. 154(b) by 864 days.

(21) Appl. No.: 12/477,022

(22) Filed: Jun. 2, 2009

(65) Prior Publication Data

US 2010/0301214 A1    Dec. 2, 2010

(51) Int. Cl.
*G01J 5/02* (2006.01)

(52) U.S. Cl.
USPC ..................................... 250/339.01

(58) Field of Classification Search
USPC ..................................... 250/339.01
See application file for complete search history.

(56) References Cited

U.S. PATENT DOCUMENTS

| | | | |
|---|---|---|---|
| 6,781,127 B1 * | 8/2004 | Wolff et al. | 250/332 |
| 6,975,225 B2 | 12/2005 | Privalov et al. | |
| 7,082,370 B2 | 7/2006 | Ardo et al. | |
| 7,938,576 B1 * | 5/2011 | Kychakoff et al. | 374/124 |
| 2005/0100193 A1 | 5/2005 | Privalov | |
| 2005/0274893 A1 * | 12/2005 | Behring et al. | 250/343 |
| 2006/0091310 A1 * | 5/2006 | Furry | 250/330 |
| 2008/0116377 A1 * | 5/2008 | Luk | 250/338.5 |

FOREIGN PATENT DOCUMENTS

| | | | |
|---|---|---|---|
| CA | 2509436 A1 * | 12/2006 | |
| EP | 1512955 B1 | 3/2005 | |
| WO | WO-2005/045775 A1 | 5/2005 | |

\* cited by examiner

*Primary Examiner* — Christine Sung
(74) *Attorney, Agent, or Firm* — Haynes and Boone, LLP

(57) ABSTRACT

An IR camera is disclosed, comprising two IR detectors for detecting a first and a second image of the imaged area. A beamsplitter is operable to split the incoming radiation into a first beam comprising a first wavelength spectrum and a second beam comprising a second wavelength spectrum different from the first wavelength spectrum. The first beam is received at the first IR detector and the second beam is received at the second IR detector. A processor is operable to calculate properties of the imaged area based on the first and the second image in relationship to each other. The information obtained may be used, for example, to detect the presence or identity of a gas or to determine the material properties of an imaged object.

20 Claims, 5 Drawing Sheets

INFRARED CAMERA FOR GAS DETECTION

BACKGROUND

1. Field

The present invention relates to an infrared ("IR") camera and particularly to methods of using an IR camera for detecting a gas.

2. Related Art

IR cameras are used for a number of different applications. There is a potential for using IR cameras in, for example, gas detection, or the determination of properties such as the material used in an imaged object.

U.S. Pat. No. 7,082,370 discloses a method of gas detection using three different configurations of an IR camera. In a first configuration the camera is used together with a split-mirror telescope. In front of one part of the telescope a gas correlation cell filled with a high concentration of the gas is mounted. The other part of the telescope gives a direct image. In another embodiment, two IR cameras are used together, and the gas correlation cell is mounted in front of the detector of one of the two cameras. In a third embodiment the gas correlation cell is arranged to be moved in and out of the optical path of one IR camera. In all three cases the gas correlation cell effectively acts as a band rejection filter for the absorption wavelength of the gas. Through image processing of the two images, an image showing the gas's contribution to the image can be obtained.

SUMMARY

Embodiments of the invention enable more advanced imaging functions in an IR camera.

In one aspect the invention relates to an IR camera comprising
- an optical system for receiving and focusing incoming radiation in a full wavelength range from an imaged area
- a beamsplitter arranged to split the incoming radiation into a first beam comprising a first wavelength spectrum and a second beam comprising a second wavelength spectrum different from the first wavelength spectrum
- a first IR detector for receiving the first beam and for detecting a first image of the imaged area based on at least a part of the incoming radiation
- a second IR detector for receiving the second beam and detecting a second image of the imaged area
- a processor for calculating properties of the imaged area based on the first and the second images in relationship to each other.

The invention also relates to a method of using an IR camera, comprising
- receiving in an IR camera incoming radiation in the IR wavelength range from an imaged area
- splitting the incoming radiation into a first beam in a first wavelength range and a second beam in a second wavelength range
- receiving the first beam at a first detector of the IR camera to detect a first image and receiving the second beam at a second detector of the IR camera to detect a second image
- performing calculations regarding the imaged area based on the relationship between the first and second image.

The use of a beamsplitter to split the incoming radiation into two parts enables a compact solution for a camera having two detectors for registering two images of the same scene. The images may be different in some aspect regarding the contribution from different parts of the spectrum to the image. Comparisons between the images can be used to obtain additional information about the imaged area.

The use of one or more beamsplitters with filter functions in combination with two or more detectors also enables a number of other functions, some of which will be discussed below.

In one exemplary embodiment, an IR camera has two or more detectors and one or more beamsplitters that may be used to improve the accuracy of measurements made by the camera based upon the wavelength dependency of the detector response. The wavelength dependency may be achieved with different detectors having different spectral properties, or with filters having different bandpass ranges placed in front of the detectors. According to optional embodiments of the invention, the detectors are of the same type, and the beamsplitter has filter properties that ensure that the two detectors receive different signals with respect to at least a portion of the complete wavelength range of the detectors.

According to another embodiment, the wavelength dependency of the emissivity factor can be used to determine the properties of the material of the imaged object. For example, the emissivity factor is wavelength-dependent in many materials. By arranging the two detectors to detect different parts of the wavelength spectrum, the total energy in each of the different parts of the wavelength spectrum can be determined. The total energies may be used to determine the relationship between emissivity factors for different wavelength ranges. If the temperature of the object is known, the emissivity factors themselves can be determined. Information about the different emissivity factors may be used to determine properties of the material.

According to another embodiment, a camera has two detectors and a beamsplitter that may be used to detect the presence and identity of a gas in the imaged area. This takes advantage of the property of the gas absorbing radiation according to a specific absorption spectrum in a specific wavelength range. Therefore, if any gas is present in the imaged area, the gas will influence the radiation in its absorption spectrum. In this case the beamsplitter is arranged to split the incoming IR radiation so that the specific wavelength range associated with the absorption spectrum of the gas is represented differently in the two images.

The camera may be constructed so that the beamsplitter may be easily changed. This enables the use of different beamsplitters for different applications. For example, different beamsplitters adapted for the absorption spectra of different gases may be used so that the same camera may detect a number of different gases having different absorption spectra. This may be achieved by arranging a number of beamsplitters in the camera so that they can be translated or rotated into and out of position between the optical system and the detectors. Alternatively, or in addition to this, the camera may be arranged so that a beamsplitter can be removed from the camera and replaced by another beamsplitter.

DETAILED DESCRIPTION

The following description is presented to enable a person of ordinary skill in the art to make and use the subject technology. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the subject technology. Thus, the present technology is not intended to be limited to the examples described herein and shown, but is to be accorded the scope consistent with the claims.

Figure 1:
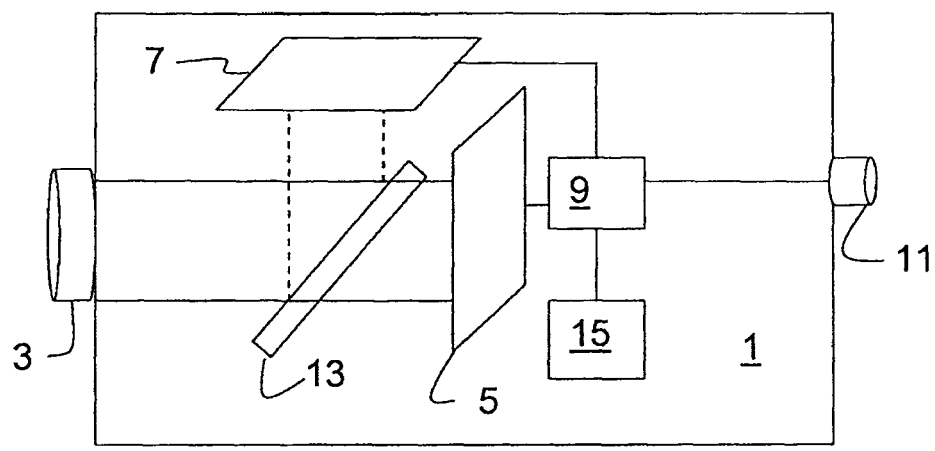
FIG. 1 illustrates schematically a camera according to an embodiment of the invention.

FIG. 1 illustrates an IR camera according to an embodiment of the invention. IR camera 1 may be used in a number of different applications, some of which will be discussed below.

IR camera 1 comprises optical system 3 for capturing and focusing incoming radiation in the IR wavelength range. The optical system comprises one or more lenses, focusing optics, and possibly other components that would be recognized by one skilled in the art as appropriate to implement the system. The camera further comprises first IR detector, 5, for detecting incoming IR radiation and second IR detector, 7, for detecting incoming IR radiation. IR detectors 5 and 7 are connected to processor 9 that performs signal processing as known in the art to provide an image that may be displayed to a user through viewfinder 11 and/or in any other way.

According to the embodiment, camera 1 also comprises beamsplitter 13 arranged in the optical path between optical system 3 and detectors 5 and 7. Beamsplitter 13, detector 5, and detector 7 are arranged relative to each other so that beamsplitter 13 will split incoming radiation received through optical system 3 into a transmitted part that will be received by the first detector, 5, and a reflected part that will be received by the second detector, 7.

IR camera 1 has one or more memory devices, 15, connected to processor 9 for storing system parameters and computer programs to be used by processor 9, as well as image data from registered images.

Beamsplitter 13 may be implemented as a pass-band filter around a suitable wavelength, in which one part of the split beam contains energy from the pass-band and the other part does not.

IR camera 1 may also have a visual imaging part. In this case, the image information related to the amplified gas may be presented within a visual image by means of fusion or blending. Further, information related to other functions may be presented in the image. For example, as will be discussed below, the camera may be used to detect the emissivity factor, to calculate the relationship between emissivity factors, or to determine the properties of the material of the imaged object. The information related to these findings may be displayed in the image.

Detectors 5 and 7 may be cooled or uncooled detectors, or one of each. Cooled detectors are more expensive and require more power than uncooled detectors. On the other hand, cooled detectors are more sensitive than uncooled detectors and therefore generally provide better images. The use of cooled detectors also enables the use of cooled filters. A filter can optionally be placed between beamsplitter 13 and IR detector 5. The filter may be a cooled filter, assuming that detector 5 is a cooled detector. Of course a cooled or uncooled filter may also be arranged between beamsplitter 13 and detector 7. Using a cooled filter may be advantageous to reduce the radiation emitted from the filter itself. This will in turn reduce the noise in the image.

It will be suitable in some applications, therefore, to use a cooled detector for the detector positioned to receive a narrow part of the wavelength range and an uncooled detector positioned to receive the remaining part of the wavelength range. This results in better sensitivity in the part of the wavelength range that is of particular interest, for example, the absorption wavelengths of a particular gas. At the same time there are cost and energy benefits of using an uncooled detector for the remaining part of the wavelength spectrum.

On the other hand, using two detectors of the same type has the advantage that the detector characteristics will be similar, making it easier to compare the images generated by the two detectors.

According to an embodiment, an IR camera is operable to detect a gas. A beamsplitter is positioned to split the incoming radiation into two beams so that the incoming radiation in the wavelength range of the absorption spectrum of the gas constitutes a different fraction of the total radiation in the first and the second beams. In this way the incoming radiation in the two images produced by the two beams can be compared in the wavelength range of the gas, and the presence and identity of a gas can be determined. The beamsplitter may be implemented as a pass-band filter around a suitable wavelength, such as the wavelength range of the gas. The first image will then comprise the gas and the background whereas the second image will comprise only the background either without the contribution from the gas or with only a part of the contribution from the gas.

For a gas with a broad absorption spectrum the filter may be selected so that the radiation from the wavelength range of the gas is maximized on one detector and minimized on the other detector. By subtracting the images generated by the two detectors, after the necessary image processing, the gas will appear clearly in the image.

Figure 2:
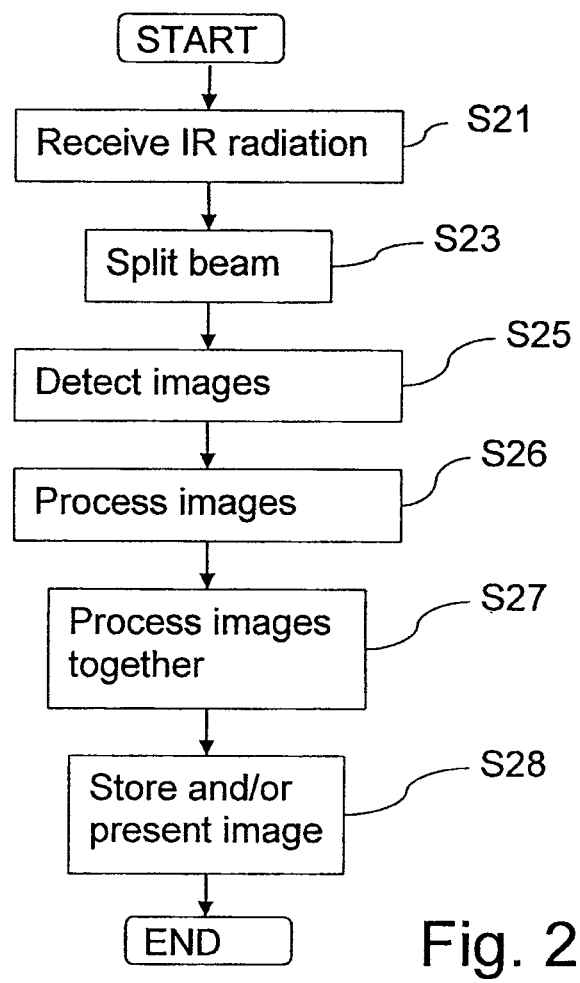
FIG. 2 is a flow chart of a method according to an embodiment of the invention.

FIG. 2 is a flow chart of a method according to an exemplary embodiment of the invention in which the IR camera is used to detect the presence and identity of a gas in the imaged area. As mentioned above, the gas has an absorption spectrum in part of the IR spectrum. Thus, the gas will affect the image for the wavelengths of the absorption spectrum.

In step S21, incoming IR radiation is received through the optical system of an IR camera.

In step S23, the incoming IR radiation is divided into a first beam that is focused onto a first detector and a second beam that is focused onto a second detector. A beamsplitter may perform the division. The beamsplitter divides the IR radiation so that the contribution of the incoming radiation in the wavelength range of the gas absorption spectrum relative to the full wavelength range is not the same in the two beams. For example, the beamsplitter may be a pass-band filter that forwards the full wavelength range except the gas absorption spectrum to the first detector and only the wavelengths in the gas absorption spectrum to the second detector.

In step S25, a first image is detected by the first detector and a second image is detected by the second detector.

In step 26, after conventional image processing, one or both of the images are processed to enable them to be compared, or processed together, in step S27.

In step S27, the first and second images are processed together to obtain the information related to the presence and identity of the gas. This may involve processing the images together so that the gas becomes more visible in the image resulting from the processing as compared to a single IR image of the image area.

In step S28, the image resulting from the processing is presented to a user and/or stored in a memory.

In a simple embodiment the processing in step S27 consists of subtracting the second image from the first image. In the resulting image the wavelength components corresponding to the absorption spectrum of the gas will be enhanced. Optionally, the second image may be amplified first to match the amplitudes of the first image.

Figure 3:
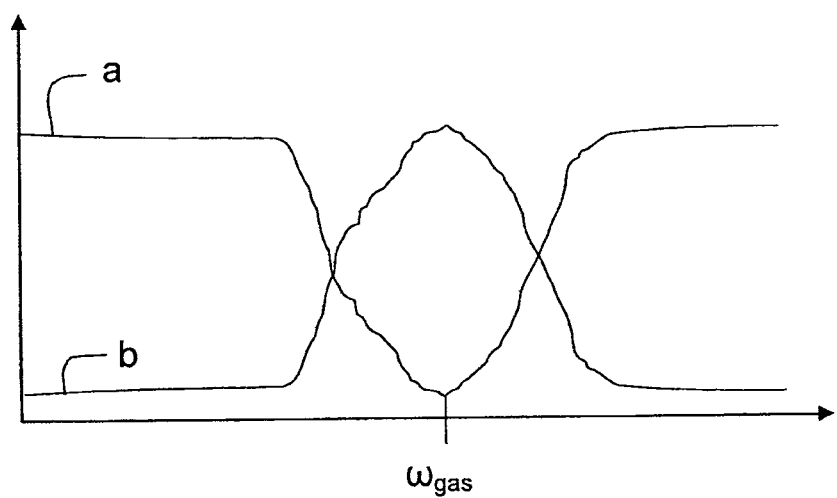
FIG. 3 is a first schematic example of the filtering function of a beamsplitter.

FIG. 3 is an example of how the wavelength spectra of the two images may look. In this example, the curve denoted "a" shows the spectrum of the first image, which includes the full wavelength range of the IR radiation except the wavelength range around the central wavelength of the gas absorption spectrum. The curve denoted "b" shows the spectrum of the second image, which mainly has a contribution from the gas absorption spectrum. The centre wavelength of the gas absorption range is marked on the x axis as $\omega_{gas}$. As can be seen, the second image, associated with curve "b", only has a contribution in the gas absorption spectrum while the contribution from the rest of the full range is close to zero. In the first image, associated with curve "a", the radiation in the gas absorption spectrum has mostly been excluded. Optionally, before comparing the images, the amplitudes of the two images may be adjusted to match each other (e.g., normalized). The adjustment may be made by adjusting the detector settings, or by signal processing of the values from one or both detectors in the processor.

After the adjustment, if performed, the second image may be subtracted from the first image to produce a resulting image in which the contribution from the gas absorption spectrum is amplified relative to the background. Alternatively, or in addition, more advanced image processing may be performed, which would be based on other indicators of the relative signal intensity of the two images, such as the ratio between them. Advanced image processing may result in the gas appearing more clearly in the image. A more detailed discussion will be given below.

Hence, this embodiment of the invention results in the relationship between the radiation in the gas absorption spectrum and the full wavelength spectrum being different in the first and second images. By properly selecting the properties of the beamsplitter, two images with this difference may be obtained. Once the two images are obtained, through appropriate processing, the gas component in the resulting image will be amplified compared to the gas component in an IR image obtained directly.

As will be understood, FIG. 3 results from a beamsplitter that is approximately an ideal filter. In practice, an ideal filter may or may not be a good approximation of a real filter. Therefore, FIG. 3 is intended to illustrate the principle of beam splitting rather than a physical reality. A person skilled in the art would know how to select filters to achieve the desired beams based on the wavelengths or frequencies that are to be filtered out. Additionally, FIG. 3 is intended to illustrate that filter choice may cause the radiation contribution of a wavelength range to be different on the two detectors.

The following discussion is based on the spectra shown in FIG. 3. In mathematical terms, the first image, $S_1$, having a spectral response that essentially excludes the gas absorption spectra ($\omega G$), represents the background radiation, B. That is:

$$S_1 = B \tag{1}$$

The second image, $S_2$, represents the radiation, G, in the gas absorption spectrum. In the absence of any gas, an ideal $S_2$ represents an attenuated level of the background radiation, B. This is because in most cases the level of IR radiation within the gas absorption spectrum will be comparable to the level outside the gas absorption spectrum. $S_2$ will be attenuated because the gas absorption spectrum is typically more narrow and thus contains less total energy than the spectrum outside of the gas absorption spectrum.

However, in practice, the signal from the detector producing $S_2$ is not just an attenuated version of the signal from the detector that images $S_1$. This is because factors such as the temperature and the material of the imaged object may affect the ratio in signal between the two detectors.

For example, in one case, the level of background radiation in $S_2$, in absence of any gas, will be ¹⁄₁₀₀₀ times B. Therefore in this example:

$$S_2 = B/1000 \tag{2}$$

The presence of gas within the field of view of the IR camera will, ideally, affect only the signal of the second detector but not the signal of the first detector, since the first detector is not sensitive to the gas absorption wavelengths. Thus, if gas is present, the signal from the second detector can be written as:

$$S_2 = B/1000 + \Delta Gas \tag{2a}$$

$\Delta$Gas can be either a positive or a negative contribution to the total signal level because the effect the gas has on the signal depends on many factors, such as the background temperature, gas temperature, and gas concentration.

To normalize the second image $S_2$ to a normalized image $S_2'$, the value of $S_2$ is multiplied by 1000. This gives:

$$S_2' = 1000 \Delta Gas + B \tag{3}$$

As discussed in an earlier embodiment, one method of processing the first and second images would be to subtract $S_1$ from $S_2'$ which would result in a final image $S_{final}$ given by:

$$S_{final} = 1000 \Delta Gas \tag{4}$$

Any suitable image processing method known in the art may be used. The skilled person is aware of a number of such methods.

Figure 4:
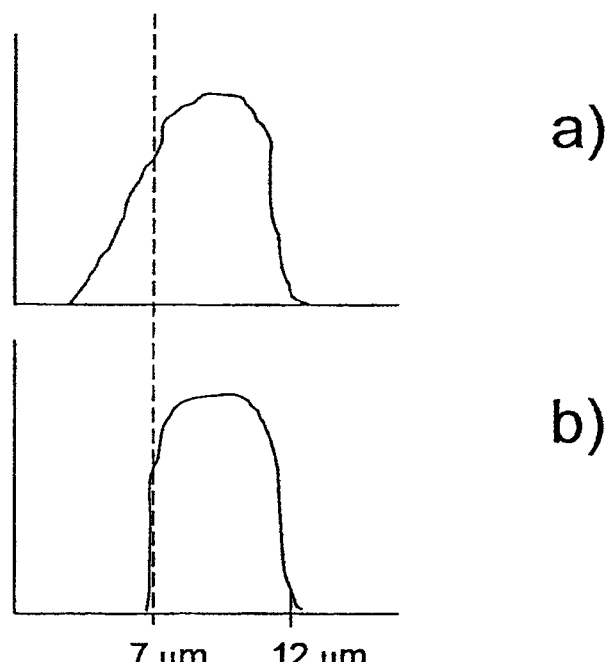
FIG. 4 illustrates the response of a detector.

FIG. 4 illustrates the spectral response of a detector. As an example, the detector is assumed to absorb in the spectrum between 7 micrometers and 12 micrometers. In "a" the absorption of the detector itself is shown. Since the detector is not perfect, there is some absorption outside of the desired spectrum as well. In "b" a situation in which a filter is arranged in front of the detector is shown. The filter is arranged to clip wavelengths lower than 7 micrometers. This will improve the left flank of the absorption curve by more effectively filtering the wavelengths below 7 micrometers. As a result, the detector will absorb in the spectrum from 7 micrometers to 12 micrometers with some absorption in the spectrum immediately below 7 micrometers and immediately above 12 micrometers.

Figure 5:
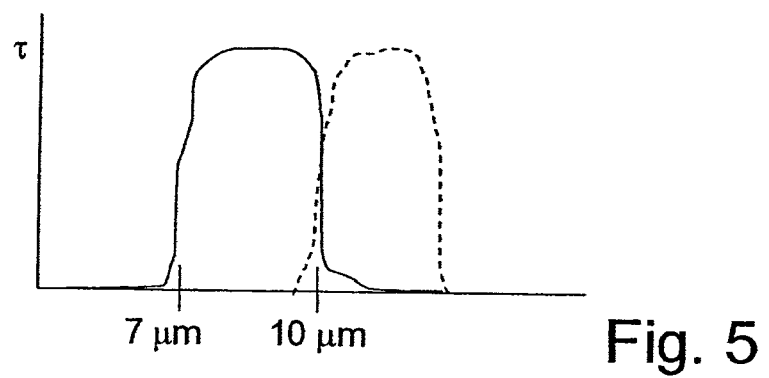
FIG. 5 illustrates the response of two detectors.

FIG. 5 illustrates the situation with two detectors of the type shown in FIG. 4 and a beamsplitter arranged to reflect radiation between the wavelengths 7 micrometers and 10 micrometers in a configuration as shown in camera 1 of FIG. 1. As a result, the first detector will receive the radiation outside of this wavelength range. Since the first detector can absorb radiation between 7 and 12 micrometers, the first detector will absorb the radiation it receives within this wavelength range, that is, between 10 and 12 micrometers. The second detector will receive and detect the wavelengths reflected by the beamsplitter, that is, the wavelengths between 7 and 10 micrometers.

Figure 6:
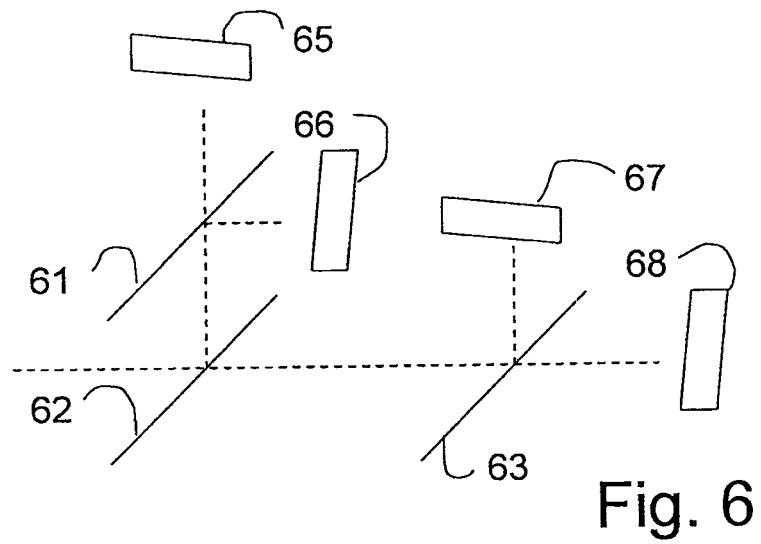
FIG. 6 is a first schematic illustration of a configuration involving several beamsplitters and several detectors.

FIG. 6 illustrates a first example configuration involving several detectors. In FIG. 6, four detectors and three beamsplitters are shown in a branch configuration. A first beamsplitter, 62, is arranged to reflect radiation to a second beamsplitter, 61, and transmit the remaining radiation to a third beamsplitter, 63. The second beamsplitter, 61, is arranged to reflect radiation to a first detector, 66, and transmit radiation to a second detector, 65. The third beamsplitter, 63, is arranged to reflect radiation to a third detector, 67, and transmit radiation to a fourth detector, 68.

As will be understood by the skilled person, by selecting the filtering properties of the beamsplitters in suitable ways, the detectors may detect different interesting portions of the full wavelength range. For example, detectors 65 and 67 may receive radiation around two different absorption wavelength spectra of a particular gas while detectors 66 and 68 may receive radiation outside of these absorption spectra. This may provide more reliable information about the presence or identity of a gas. Alternatively, detectors 65 and 67 may receive radiation around the absorption spectra of two different gases to enable the detection of two different gases at the same time using the same camera.

Figure 7:
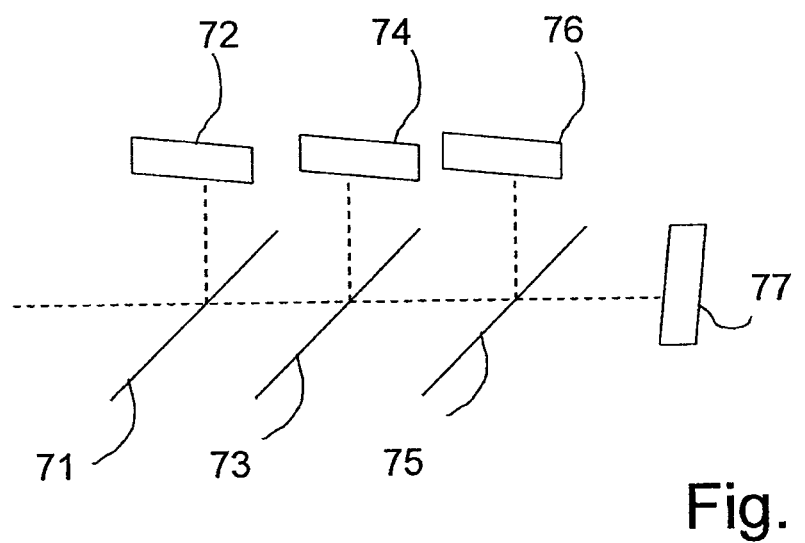
FIG. 7 is a second schematic illustration of a configuration involving several beamsplitters and several detectors.

FIG. 7 illustrates a second example configuration involving several detectors. Three beamsplitters are arranged in series so that a first beamsplitter, 71, reflects radiation to a first detector, 72, and transmits radiation to a second beamsplitter, 73. The second beamsplitter, 73, reflects radiation to a second detector, 74, and transmits radiation to a third beamsplitter, 75. The third beamsplitter, 75, reflects radiation to a third detector, 76, and transmits radiation to a fourth detector, 77.

In FIG. 7, the filtering properties of the beamsplitters may be selected so that the detectors may detect different interesting portions of the full wavelength range. For example, each of beamsplitters 71, 73, and 75 may reflect a portion of the wavelength range corresponding to an absorption spectrum of a gas while transmitting the remaining portion. In this way detectors 72, 74, and 76 will receive and detect radiation in spectral portions of interest, whereas detector 77 will receive the radiation outside of these portions of interest. The spectral portions reflected by beamsplitters 71, 73, and 75 may be selected as different absorption ranges for one gas or corresponding to absorption spectra of two or three different gases.

Hence, the configurations shown in FIG. 6 and FIG. 7 may be designed to obtain a fingerprint to identify a particular gas by detecting radiation in different parts of the gas absorption spectrum. Alternatively, or in addition, the configurations may be designed to detect two or more gases by detecting radiation in absorption spectra of both or all gases. Of course, each of the configurations shown in FIG. 6 and FIG. 7 may be expanded to include more beamsplitters and more detectors. A combination of a serial and a branched configuration is also perceivable, of course.

The configuration of a beamsplitter and two detectors can also be used to improve the accuracy of measurements within the camera. In an exemplary embodiment of the invention, a detector registers incoming radiation within a specific wavelength range. The detector may be used to determine the total energy of the registered radiation, but it is not able to distinguish between different wavelengths within this wavelength range.

The signal $S_{measured}$ that is measured by the camera is proportional to the total energy, $E_{tot}$, of the radiation that hits the detector within its absorption range, that is:

$$S_{measured} = f(E_{tot}) \tag{5}$$

With a simplification, $E_{tot}$ is a function E of the temperature, $T_{obj}$, of the imaged object, that is:

$$E_{tot} = E(T_{obj}) \tag{6}$$

The function $f(E_{tot})$ is dependent on the IR camera function in converting the incoming radiation to a measurable digital signal. This in turn depends on several factors, such as the detector characteristic, the read-out function from the detector, and the subsequent processing of the detector signal. This function can be determined by measurements during calibration of the IR camera.

A more correct $E_{tot}$ must however take into account the wavelength-dependent emissivity factor $\epsilon$ of the object, which determines the reflection and emission of an object, which gives:

$$E_{tot} = \epsilon * E(T_{obj}) + (1-\epsilon) * E(T_{refl}) \tag{7}$$

Where $T_{refl}$ is the temperature of the object whose radiation hits the surface of the object to be subsequently reflected to the IR camera. As can be seen from Eq. (7), to obtain the temperature of the object the emissivity factor $\epsilon$ and $T_{refl}$ must be known.

The function E(T) can be described as the integration of the product of Planck's radiation law and the absorption spectrum of the IR camera, that is:

$$E(T) = \int_0^\infty \text{detector\_response}(\lambda) * \text{Planck}(\lambda, T) \, d\lambda \tag{8}$$

Where Planck denotes Planck's law of radiation. The function E(T) may be approximated by means of other methods that do not require integration. Such methods are known in the art.

During calibration of a camera, the different values of the function E(T) can be measured, as well as Eq. (5). The measured values are fit to a curve, for example by means of a polynomial fit giving the best possible polynomial parameters based on the measured values, or by another suitable mathematical function. This means that the function E(T) will be known to the camera, which enables the conversion of signal level to temperature. During operation of the camera a measured signal level can be converted to the temperature of an object using Eq. (9):

$$T_{obj} = E^{-1}\left(\frac{E_{tot} - (1-\varepsilon) * E(T_{refl})}{\varepsilon}\right) \tag{9}$$

To obtain the object's temperature, $T_{obj}$, from this equation, both $\epsilon$ and $T_{refl}$ must be known. This is normally achieved by the user feeding these values into the camera.

When two IR detectors are used, as according to an embodiment of the invention, two different equations for the total energy can be obtained, for different wavelength ranges, according to the following:

$$E_{Tot1} = \epsilon * E_1(T_{obj}) + (1-\epsilon) * E_1(T_{refl}) \tag{10}$$

$$E_{Tot2} = \epsilon * E_2(T_{obj}) + (1-\epsilon) * E_2(T_{refl}) \tag{11}$$

Where $E_{Tot1}$ and $E_{Tot2}$ are the total energy registered by the first and the second detector, respectively, within the wavelength range it is arranged to detect. For this application it is assumed that the emissivity is constant throughout the wavelength range concerned.

The functions $E_1(T)$ and $E_2(T)$ can be obtained from Eq. (8) in the same way as with one detector, but will differ if they have different spectral properties. Both functions can be measured during calibration of the camera using the same method as used for one detector.

According to an embodiment of the invention, the functions $E_1(T)$ and $E_2(T)$ representing the energy registered by the first and the second detector, respectively, are determined during calibration. Thus, the functions $E_1(T)$ and $E_2(T)$ can be known for a camera having two detectors with different spectral properties.

Hence, with two detectors, the two different equations (10) and (11) are obtained, which allows two unknowns to be determined. Thus, the camera is able to determine the values for the object's temperature $T_{obj}$ and the emissivity $\epsilon$, if a value for $T_{refl}$ is available. A suitable value for $T_{refl}$ can be entered into the camera by an operator. Using the wrong emissivity value severely impairs measurements. Therefore, improving the accuracy of the emissivity factor used by the camera will significantly reduce measurement errors.

According to another embodiment of the invention, an IR camera can be used to determine the properties of the material of the object. This can be done by exploiting the fact that the emissivity factor of the material is often wavelength-dependent. Therefore, the emissivity factor in the first wavelength range will be denoted $\epsilon_1$ and the emissivity factor in the second wavelength range will be denoted $\epsilon_2$.

Assuming that the emissivity factors $\epsilon_1$ and $\epsilon_2$ in the images detected by the two detectors as defined in Eqs. (10) and (11) are not the same, they can be determined, provided that the temperature, $T_{obj}$, of the imaged object is known.

If the object temperature, $T_{obj}$, is not known, the ratio, k, between the emissivity factors $\epsilon_1$ and $\epsilon_2$ can be determined:

$$k = \epsilon_1 / \epsilon_2 \quad (12)$$

By entering a value for $\epsilon_1$, $\epsilon_2$ can be expressed as:

$$\epsilon_2 = k * \epsilon_1 \quad (13)$$

This enables k and $T_{obj}$ to be determined by means of Eq. (10) and (11), although the absolute value of the emissivity factors $\epsilon_1$ and $\epsilon_2$ cannot be determined.

It will be appreciated that, for clarity purposes, the above description has described embodiments of the technology with reference to different functional units. However, it will be apparent that any suitable distribution of functionality between different functional units, processors or domains may be used without detracting from the technology. For example, functionality illustrated to be performed by a separate beamsplitter and filter may be performed by a beamsplitter with a built in filter. Hence, references to specific functional units are only to be seen as references to suitable means for providing the described functionality, rather than indicative of a strict logical or physical structure or organization.

Although the current technology has been described in connection with some embodiments, it is not intended to be limited to the specific form set forth herein. Rather, the scope of the current invention is limited only by the claims. Additionally, although a feature may appear to be described in connection with particular embodiments, one skilled in the art would recognize that various features of the described embodiments may be combined.

Furthermore, although individually listed, a plurality of means, elements or method steps may be implemented by, for example, a single unit or processor. Additionally, although individual features may be included in different claims, these may possibly be advantageously combined, and the inclusion in different claims does not imply that a combination of features is not feasible and/or advantageous. Also, the inclusion of a feature in one category of claims does not imply a limitation to this category, but rather the feature may be equally applicable to other claim categories, as appropriate.

Moreover, it will be appreciated that various modifications and alterations may be made by those skilled in the art without departing from the spirit and scope of the invention. The current invention is not to be limited by the foregoing illustrative details, but is to be defined according to the claims.

What is claimed is:

1. An infrared ("IR") camera comprising:
   an optical system configured to receive incoming radiation in an IR wavelength range from an imaged area;
   a first thermal IR detector;
   a second thermal IR detector;
   a first beamsplitter configured to transmit a first wavelength spectrum and reflect a second wavelength spectrum,
      wherein the incoming radiation received through the optical system is split by the first beamsplitter into a first beam having the first wavelength spectrum that is transmitted through the first beamsplitter and a second beam having the second wavelength spectrum that is reflected from the first beamsplitter and is of a different wavelength spectrum than the first wavelength spectrum,
      wherein the first and second beam represent a same scene of the imaged area,
      wherein the first thermal IR detector is configured to receive the first beam and detect a first image of the imaged area based on the first beam, and
      wherein the second thermal IR detector is configured to receive the second beam and detect a second image of the imaged area based on the second beam;
   a processor operable to calculate properties of the imaged area based on a relationship of the first and the second images; and
   a display, coupled to the processor, for viewing by a user of the camera,
      wherein the camera is operable to detect a presence of a gas in the imaged area by comparing the second image to the first image to obtain a gas image indicating the presence of the gas in the image area, said gas having a particular gas wavelength range,
      wherein the first beamsplitter is configured to split the incoming radiation so that the relationship between the gas wavelength range and the incoming IR wavelength range in the first beam is different from the relationship between the gas wavelength range and the incoming IR wavelength range in the second beam, and
      wherein the camera is configured to present the obtained gas image on the display for viewing by the user.

2. The IR camera according to claim 1, wherein the first beamsplitter is operable to split the incoming radiation so that the first image has a stronger contribution of radiation in the wavelength range of the gas as compared to the contribution of radiation in the wavelength range of the gas in the second image and the second image has a stronger contribution of radiation outside the frequency spectrum of the gas as compared to the contribution of radiation in the frequency spectrum of the gas in the second image.

3. The IR camera according to claim 1, wherein the processor is operable to determine a first total energy registered by the first thermal IR detector, a second total energy registered by the second thermal IR detector, and a value of the temperature of an imaged object or an emissivity factor for the object, based on the first total energy and the second total energy.

4. The IR camera according to claim 1, wherein the processor is operable to determine a first total energy registered by the first thermal IR detector in the first wavelength spectrum, a second total energy registered by the second thermal IR detector in the second wavelength spectrum, and a value representative of a first emissivity factor of an imaged object based on the first total energy and a value representative of a second emissivity factor based on the second total energy.

5. The IR camera according to claim 4, wherein the processor is operable to determine the first emissivity factor and the second emissivity factor based on the first and second total energy, respectively, and a temperature of the imaged object.

6. The IR camera according to claim 4, wherein the processor is operable to determine a relationship between the first emissivity factor and the second emissivity factor.

7. The IR camera according to claim 1, further comprising:
a second beamsplitter configured to further split the first beam from the first beamsplitter into a reflected part having a third wavelength spectrum and a transmitted part having a fourth wavelength spectrum different from the third wavelength spectrum; and
a third thermal IR detector configured to receive the reflected part of the first beam and detect a third image of the imaged area based on the reflected part of the first beam,
wherein the first thermal IR detector is configured to receive the transmitted part of the first beam to detect the first image of the imaged area.

8. The IR camera according to claim 1, further comprising:
a second beamsplitter configured to further split the second beam from the first beamsplitter into a reflected part having a third wavelength spectrum and a transmitted part having a fourth wavelength spectrum different from the third wavelength spectrum; and
a third thermal IR detector configured to receive the reflected part of the second beam and detect a third image of the imaged area based on the reflected part of the second beam,
wherein the second thermal IR detector is configured to receive the transmitted part of the second beam to detect the second image of the imaged area.

9. The IR camera according to claim 8, wherein each beamsplitter is selectable according to a corresponding type of gas to be detected in the imaged area.

10. The IR camera according to claim 1,
further comprising one or more additional beamsplitters for splitting a beam into a reflected part and a transmitted part respectively having a different wavelength spectrum, wherein the first beamsplitter and the one or more additional beamsplitters are configured to selectively translate or rotate into and out of an optical path between the optical system and the thermal IR detectors.

11. A method of using an infrared ("IR") camera, the method comprising:
receiving, through an optical system of the IR camera, incoming radiation in an IR wavelength range from an imaged area;
splitting the incoming radiation with a first beamsplitter into a first beam and a second beam based on a wavelength range of a gas to detect, by transmitting a first wavelength spectrum of the incoming radiation through the first beamsplitter as the first beam and by reflecting a second wavelength spectrum of the incoming radiation with the first beamsplitter as the second beam,
wherein the first wavelength spectrum is of a different wavelength spectrum than the second wavelength spectrum, and
wherein the first and the second beams represent a same scene of the imaged area;
receiving the first beam at first thermal IR detector of the IR camera to detect a first image;
receiving the second beam at a second thermal IR detector of the TR camera to detect a second image; and
performing calculations regarding the imaged area based on a relationship between the first and second images to detect a presence of a gas in the imaged area by comparing the second image to the first image to obtain a gas image indicating the presence of the gas in the imaged area; and
displaying the obtained gas image.

12. A method according to claim 11, wherein the second wavelength spectrum excludes the wavelength range of the gas and the wavelength range of the gas is a subset of the first wavelength spectrum.

13. The method according to claim 12, further comprising selecting the first beamsplitter from a plurality of different beamsplitters, wherein the first beamsplitter is selected to perform the splitting of the incoming radiation according to a corresponding type of gas to be detected.

14. The method according to claim 11 further comprising:
obtaining a visual image of the area; and
fusing the gas image with the visual image.

15. The method according to claim 11, further comprising:
determining a first total energy registered by the first thermal IR detector;
determining a second total energy registered by the second thermal IR detector; and
determining a value of the temperature of an imaged object or an emissivity factor for the object, based on the first total energy and the second total energy.

16. The method according to claim 11, further comprising:
determining a first total energy registered by the first thermal IR detector in the first wavelength spectrum;
determining a second total energy registered by the second thermal IR detector in the second wavelength spectrum; and
determining a value representative of a first emissivity factor of an imaged object based on the first total energy and a value representative of a second emissivity factor based on the second total energy.

17. The method according to claim 16, wherein determining the first emissivity factor and the second emissivity factor based on the first and second total energy, respectively, is also based on a temperature of the object.

18. The method according to claim 16, further comprising:
determining a relationship between the first emissivity factor and the second emissivity factor.

19. The method according to claim 11, further comprising:
selecting from the first beamsplitter and at least a second beamsplitter to perform the splitting of the incoming radiation according to a corresponding type of gas to be detected; and
determining if the corresponding type of gas is present in the imaged area based on the performing.

20. The method according to claim 11, further comprising:
splitting the first beam from the first beamsplitter into a reflected part having a third wavelength spectrum and a transmitted part having a fourth wavelength spectrum different from the third wavelength spectrum; and
receiving the reflected part of the first beam at a third thermal IR detector of the IR camera to detect a third image of the imaged area based on the reflected part of the first beam, wherein the receiving the first beam to detect the first image is by receiving the transmitted part of the first beam from the second beamsplitter.

* * * * *